United States Patent
Shin et al.

(10) Patent No.: US 9,782,213 B2
(45) Date of Patent: *Oct. 10, 2017

(54) OVERLAPPING BIPOLAR ELECTRODE FOR HIGH-FREQUENCY HEAT TREATMENT

(71) Applicant: STARmed Co., Ltd, Goyang-si (KR)

(72) Inventors: Kyung Min Shin, Seoul (KR); Kyung Hoon Shin, Gimpo-si (KR); Dong Un Kim, Gimpo-si (KR)

(73) Assignee: STARmed Co., Ltd. (KR)

( * ) Notice: Subject to any disclaimer, the term of this patent is extended or adjusted under 35 U.S.C. 154(b) by 435 days.

This patent is subject to a terminal disclaimer.

(21) Appl. No.: 14/401,880

(22) PCT Filed: May 10, 2013

(86) PCT No.: PCT/KR2013/004143
§ 371 (c)(1),
(2) Date: Nov. 18, 2014

(87) PCT Pub. No.: WO2013/172600
PCT Pub. Date: Nov. 21, 2013

(65) Prior Publication Data
US 2015/0133916 A1 May 14, 2015

(30) Foreign Application Priority Data

May 18, 2012 (KR) .................. 10-2012-0053127

(51) Int. Cl.
*A61B 18/12* (2006.01)
*A61B 18/14* (2006.01)
(Continued)

(52) U.S. Cl.
CPC .......... *A61B 18/14* (2013.01); *A61B 18/1206* (2013.01); *A61B 18/1477* (2013.01);
(Continued)

(58) Field of Classification Search
CPC . A61B 18/1206; A61B 18/14; A61B 18/1477; A61B 1/06; A61B 2018/00023;
(Continued)

(56) References Cited

U.S. PATENT DOCUMENTS

| 164,184 A | 6/1875 | Kidder |
| 5,334,193 A * | 8/1994 | Nardella ............ A61B 18/1492 606/41 |

(Continued)

FOREIGN PATENT DOCUMENTS

| CN | 1901844 | 1/2007 |
| CN | 102038565 | 5/2011 |

(Continued)

OTHER PUBLICATIONS

European Search Report dated Dec. 15, 2015 from corresponding EP application 13791420.6 (8 pages).

(Continued)

*Primary Examiner* — Daniel Fowler
(74) *Attorney, Agent, or Firm* — Anderson Gorecki LLP (57) ABSTRACT

The present invention relates to a bipolar electrode, and more particularly, to an electrode for high-frequency heat treatment capable of cauterizing and necrotizing lesions by heating the lesions, such as a cancer tissue of a body organ, with a high frequency, in particular, an overlapping bipolar electrode for high-frequency heat treatment capable of cauterizing lesions of tubular organs, such as a blood vessel, with a minimum invasion.

3 Claims, 7 Drawing Sheets

(51) Int. Cl.
*A61N 1/06* (2006.01)
*A61B 18/00* (2006.01)
*A61B 18/16* (2006.01)

(52) U.S. Cl.
CPC ............... *A61B 2018/00023* (2013.01); *A61B 2018/00529* (2013.01); *A61B 2018/00577* (2013.01); *A61B 2018/00595* (2013.01); *A61B 2018/126* (2013.01); *A61B 2018/1435* (2013.01); *A61B 2018/162* (2013.01); *A61N 1/06* (2013.01)

(58) Field of Classification Search
CPC A61B 2018/00529; A61B 2018/00577; A61B 2018/00595; A61B 2018/126; A61B 2018/1435; A61B 2018/162
See application file for complete search history.

(56) References Cited

U.S. PATENT DOCUMENTS

| | | | |
|---|---|---|---|
| 5,749,914 | A | 5/1998 | Janssen |
| 5,921,954 | A | 7/1999 | Mohr, Jr. et al. |
| 5,972,026 | A | 10/1999 | Laufer et al. |
| 6,014,589 | A | 1/2000 | Farley et al. |
| 6,139,536 | A | 10/2000 | Mikus et al. |
| 6,488,680 | B1 * | 12/2002 | Francischelli ..... A61B 18/1445 606/41 |
| 2002/0099366 | A1 | 7/2002 | Dahla et al. |
| 2003/0018362 | A1 | 1/2003 | Fellows et al. |
| 2005/0049670 | A1 | 3/2005 | Jones et al. |
| 2006/0161246 | A1 | 7/2006 | Rhim et al. |
| 2006/0276873 | A1 | 12/2006 | Sato |
| 2007/0149963 | A1 | 6/2007 | Matsukuma et al. |
| 2009/0143777 | A1 | 6/2009 | Pacey et al. |
| 2010/0191151 | A1 | 7/2010 | Kwak |
| 2011/0071515 | A1 | 3/2011 | Faure et al. |
| 2011/0202052 | A1 | 8/2011 | Gelbart et al. |
| 2011/0264085 | A1 | 10/2011 | Satake |

FOREIGN PATENT DOCUMENTS

| | | |
|---|---|---|
| EP | 1562506 | 8/2005 |
| JP | 1996-505544 | 5/1994 |
| JP | H09140807 | 6/1997 |
| JP | 2000140118 | 5/2000 |
| JP | 2006-506184 | 6/2004 |
| JP | 3848122 | 11/2006 |
| JP | 2011520488 | 7/2011 |
| WO | WO 94/11059 | 5/1994 |
| WO | WO 98/55046 | 12/1998 |
| WO | WO 01/58372 | 8/2001 |
| WO | WO 2009/121017 | 10/2009 |

OTHER PUBLICATIONS

International Search Report from corresponding PCT application PCT/KR2014/004143.

Office Action from corresponding EP Patent Application No. 13791710.

* cited by examiner

OVERLAPPING BIPOLAR ELECTRODE FOR HIGH-FREQUENCY HEAT TREATMENT

TECHNICAL FIELD

The present invention relates to a bipolar electrode, and more particularly, to an electrode for high-frequency heat treatment capable of cauterizing and necrotizing lesions by heating the lesions, such as a cancer tissue of a body organ, with a high frequency, in particular, an overlapping bipolar electrode for high-frequency heat treatment capable of cauterizing lesions of tubular organs, such as a blood vessel, with a minimum invasion.

BACKGROUND ART

Generally, cancer tissues which occur in body organs, for example, organs such as a liver are treated by a non-surgical method or a surgical operation.

In this case, the surgical operation mainly resects a body with a lesion, and as a result, the lesion becomes very wide. Therefore, the surgical operation has a problem in that a big scar remains, convalescence is required for a considerable period of time, and the like. Further, cancer tissues, and the like are likely to recur in body organs and in the case of the recurrence, a re-operation needs to perform, and therefore, the surgical operation has a problem in that pain, financial burden, and risk of a patient are increased.

As a result, the non-surgical methods, for example, transarterial chemoembolization, percutaneous ethanol injection therapy, generalized chemotheraphy, local heat therapy, and the like have been used. Among those, the local heat therapy has been known as the most effective in improving a short-term treatment outcome or a long-term survival rate.

An example of the local heat treatment may include high-frequency heat treatment, microwave cauterization, laser cauterization, and the like. Among those, the high-frequency heat treatment has been used most effectively.

Here, when the cancer tissues occur in the body organs, for example, a liver, the high-frequency heat treatment is a treatment method for cauterizing and necrotizing only the cancer tissues with high-frequency heat without performing a resection on only the cancer tissues.

To this end, an electrode apparatus for the typical high-frequency heat treatment is configured in a structure in which a ground pad as a passive electrode body generally adheres to a patient's epidermis, a needle-shaped electrode as an active electrode body is inserted into a lesion, and then the ground pad and the needle-shaped electrode are electrically connected to a high-frequency generator.

Therefore, when power is applied to the high-frequency generator, a current transfer path from an electrode to the ground pad is formed and during the transfer process, friction energy due to vibration of ions increases a temperature of tissues to induce coagulation and necrosis of tissues around a lesion.

However, since the general electrode apparatus as described above performs an operation using a monopolar needle-shaped electrode, the electrode apparatus has a problem in that a high-frequency current flowing through the ground pad attached to the patient's epidermis is not locally applied only to lesions and is applied to the whole path reaching the electrode, and therefore affects normal organs or tissues or burns the portion to which the ground pad is attached.

Figure 1:
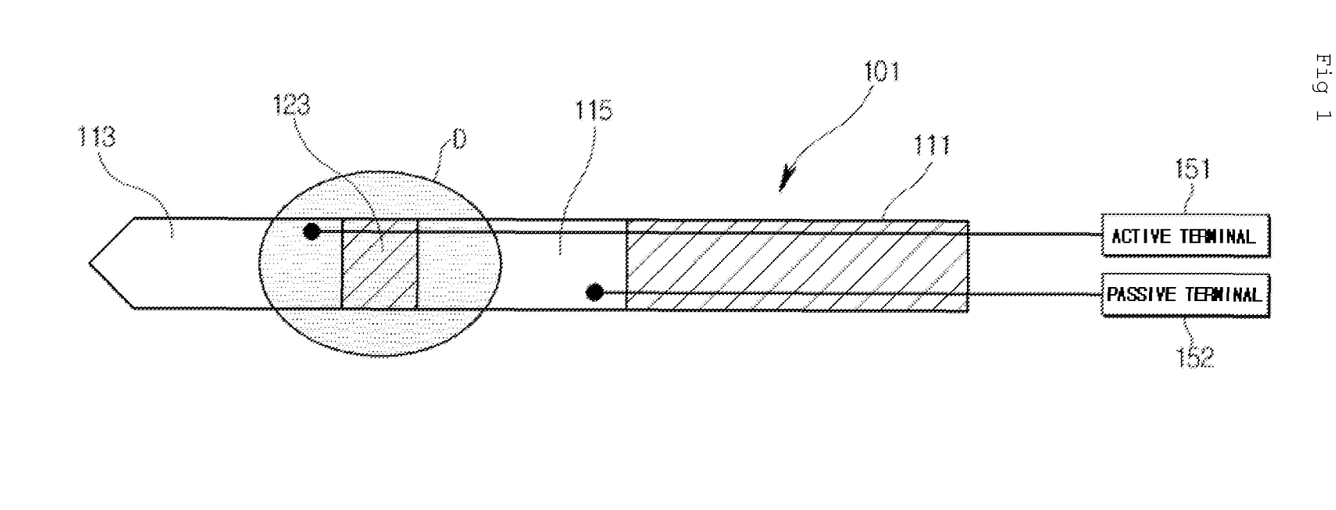
FIG. 1 is a diagram illustrating a bipolar electrode for high-frequency heat treatment according to the related art.

To solve the problem, as illustrated in FIG. 1, a needle-shaped bipolar electrode 101 which includes an active electrode body 113 disposed at a tip portion of one body 111 and a passive electrode body 115 is proposed.

As illustrated in FIG. 1, the bipolar electrode 101 has a structure in which the active electrode body 113 which disposed at a tip portion of the body 111 is connected to an active terminal 151 of a high frequency generator, the passive electrode body 115 which is disposed at a back portion of the body 111 is connected to a passive terminal 152, and an insulator part 123 is disposed between the active electrode body 113 and the passive electrode body 115, thereby radiating high frequency energy between the active electrode body 113 and the passive electrode body 115. Therefore, a path from the active electrode body 113 to the passive electrode 115 becomes very short, and as a result, a range of a body portion affected by a high frequency current may be remarkably reduced.

Figure 2:
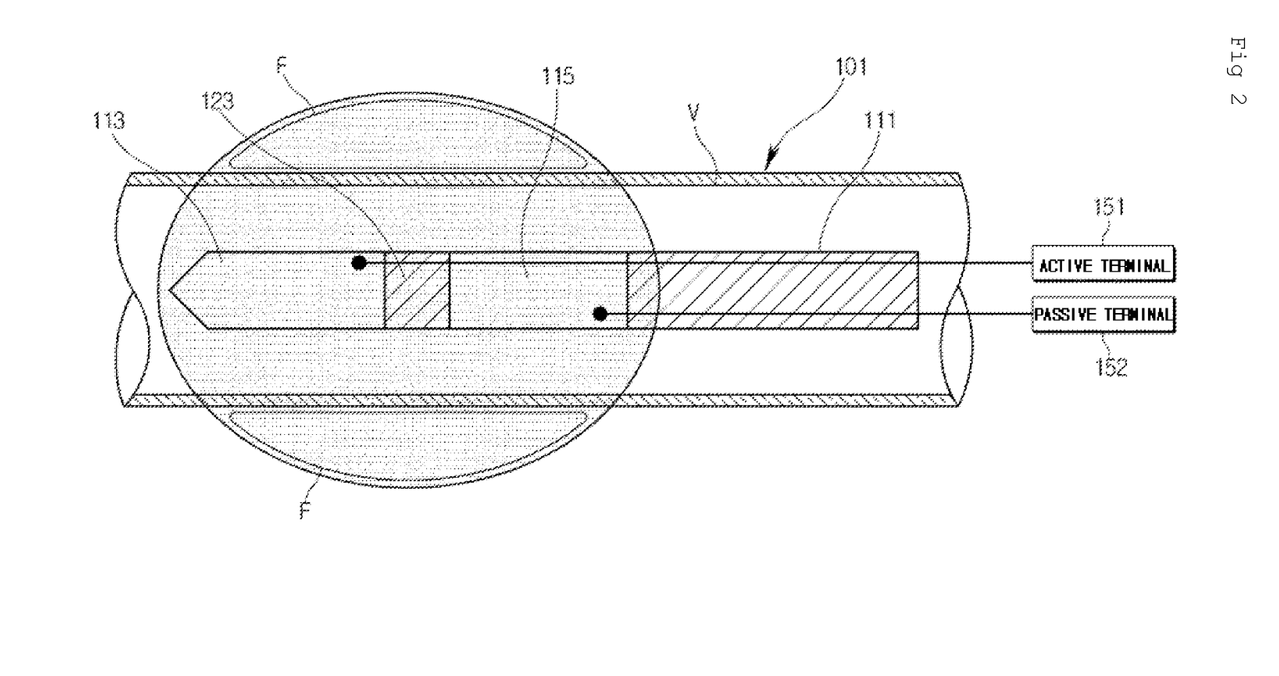
FIG. 2 is a diagram illustrating a heat generation range due to high-frequency energy radiation in an electrode illustrated in FIG. 1.

However, the typical bipolar electrode 101 generates heat generation due to high-frequency energy radiation around the insulating part 123 as represented by D in FIG. 1, such that the heat generation is extended in an oval shape around the insulating part 123 as represented by F in FIG. 2.

Therefore, when the typical bipolar electrode 101 intends to perform an operation on, in particular, a tubular tissue such as a blood vessel, the typical bipolar electrode 101 has a problem in that since the heat generation range is formed in an oval shape around the insulating part 123 but a lesion to be treated occur in a cylindrical shape along a form of the tubular tissue, the bipolar electrode 101 cauterizes and damages normal tissues around the tubular tissue at a portion (represented by F in FIG. 2) where the heat generation range around the insulating part 123 which is an intermediate point of the heat generation range in a length direction is beyond a lesion, while since the heat generation range does not reach the lesion at both end points of the heat generation range in a length direction, the bipolar electrode 101 does not cauterize the lesion and thus does not perform an effective operation.

DISCLOSURE

Technical Problem

The present invention proposes to solve the above problems, and an object of the present invention is to minimize a damage of adjacent normal tissues occurring at the time of cauterizing a lesion and improve heat treatment efficiency of an electrode, by overlappingly disposing in a spiral form a bipolar electrode on an electrode body so as to make a heat generation range, that is, a cauterization range due to high-frequency energy radiation at the time of performing an operation on, in particular, a tubular tissue such as a blood vessel maximally coincide with a lesion.

Technical Solution

To achieve the above object, according to the present invention, there is provided an overlapping bipolar electrode for high-frequency heat treatment including: a cylindrical electrode body; an active electrode body configured to be connected to one terminal of a high frequency generator while being wound from a tip portion of an outer peripheral surface of the body toward a rear end thereof in plural times; and a passive electrode body configured to be connected to the other terminal of the high frequency generator while being wound from a tip portion of an outer peripheral surface of the body toward a rear end thereof through the active electrode body in plural times.

Further, the active electrode body and the passive electrode body may be wound in a spiral form around the outer peripheral surface of the body at a constant alternating gap therebetween.

Further, the active electrode body and the passive electrode body may each include continuously overlapping concentration parts without any one electrode thereof alternating with the other electrode thereof and the concentration parts may be wound around the outer peripheral surface of the body at a denser gap than the alternating gap of the electrodes or gapless.

Further, an insulating gap may be formed between the concentration part of the any one electrode body and the concentration part of the other electrode body.

Further, the outer peripheral surface of the body corresponding to the insulating gap may be provided with an insulating part.

DETAILED DESCRIPTION OF EMBODIMENTS

Hereinafter, an overlapping bipolar electrode for high-frequency heat treatment according to an embodiment of the present invention will be described with reference to the accompanying drawings.

Figure 3:
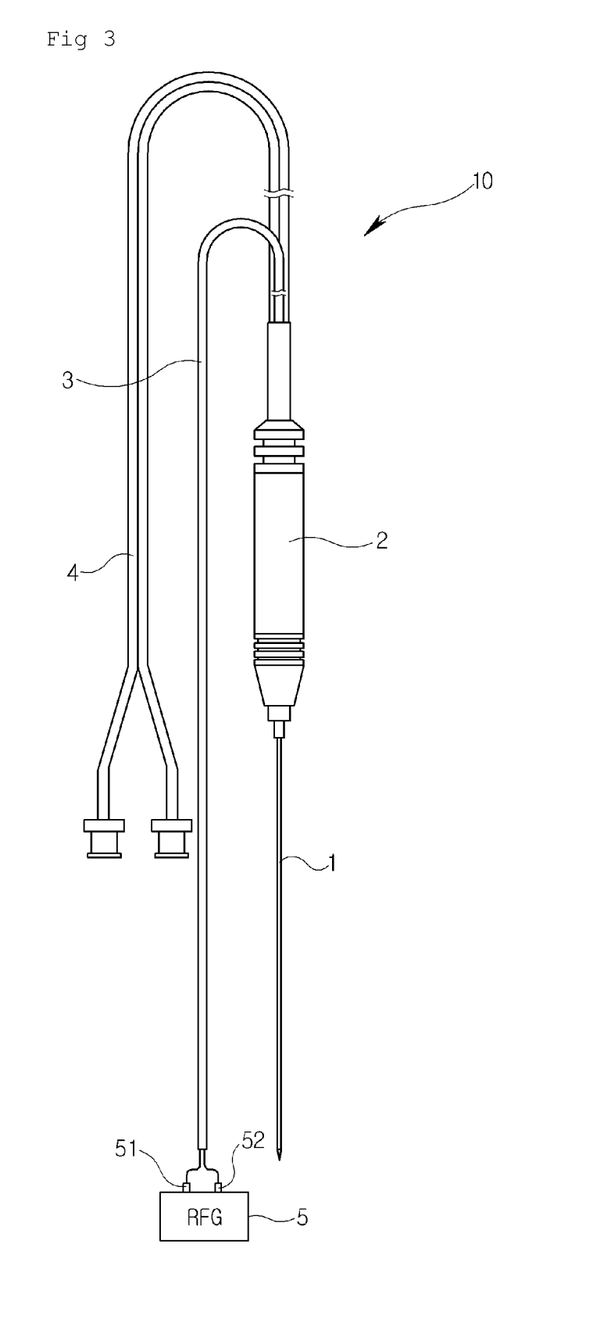
FIG. 3 is a schematic diagram illustrating an electrode apparatus for high-frequency heat treatment to which a bipolar electrode for high-frequency heat treatment according to the present invention is applied.

Since the overlapping bipolar electrode for high-frequency heat treatment according to the present invention which is illustrated in reference numeral 1 in FIG. 3 may be applied to various types of high-frequency heat treatment apparatuses as an electrode probe, the bipolar electrode radiates high frequency energy to tissues around a lesion in the state in which it is inserted into tissues around a lesion so as to serve to provide a coagulation necrosis of the tissues around the lesion.

As illustrated in FIG. 3, an electrode apparatus 10 for high-frequency heat treatment to which the electrode 1 according to the present invention is applied is configured to include a handle 2, a electrode wire 3, a cooling pipe 4, and a high frequency generator 5, in addition to the electrode 1, in which the handle 2 which is a part gripped by an operator who wants to use the electrode 1 is disposed at a back portion of the electrode 1 as illustrated in FIG. 3 and the electrode wire 3 which is a part connecting the electrode 1 to the high frequency generator 5 through the handle 3 is continued from the handle 2 to the high frequency generator 5. Further, the cooling pipe 4 is a means cooling the electrode apparatus 1 and as illustrated in FIG. 3, is connected to the handle 2 so as to supply, recover, and withdraw cooling water. Finally, the high frequency generator 5 which is an apparatus generating a high frequency alternating current is widely used for a general electrical operation and as described to be below, is configured to have a positive terminal and a negative terminal selectively connected to the active electrode body 13 or the passive electrode body 15 of the electrode 1 so as to supply the high frequency alternating current to the electrode 1.

Figure 4:
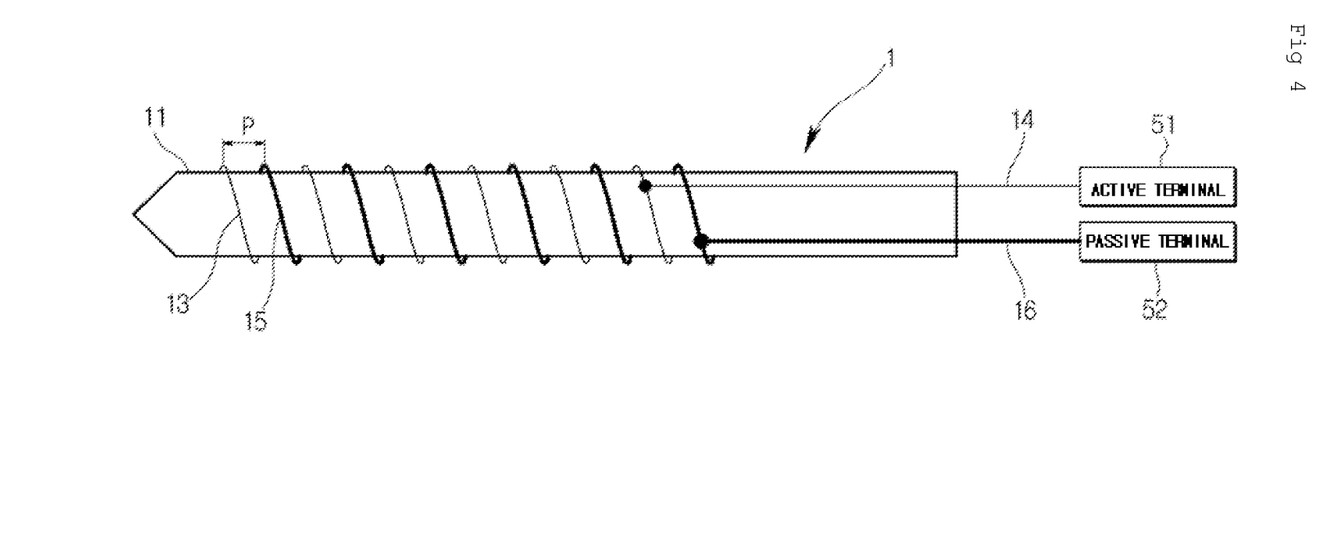
FIG. 4 is an enlarged view illustrating the electrode illustrated in FIG. 3.
Figure 5:
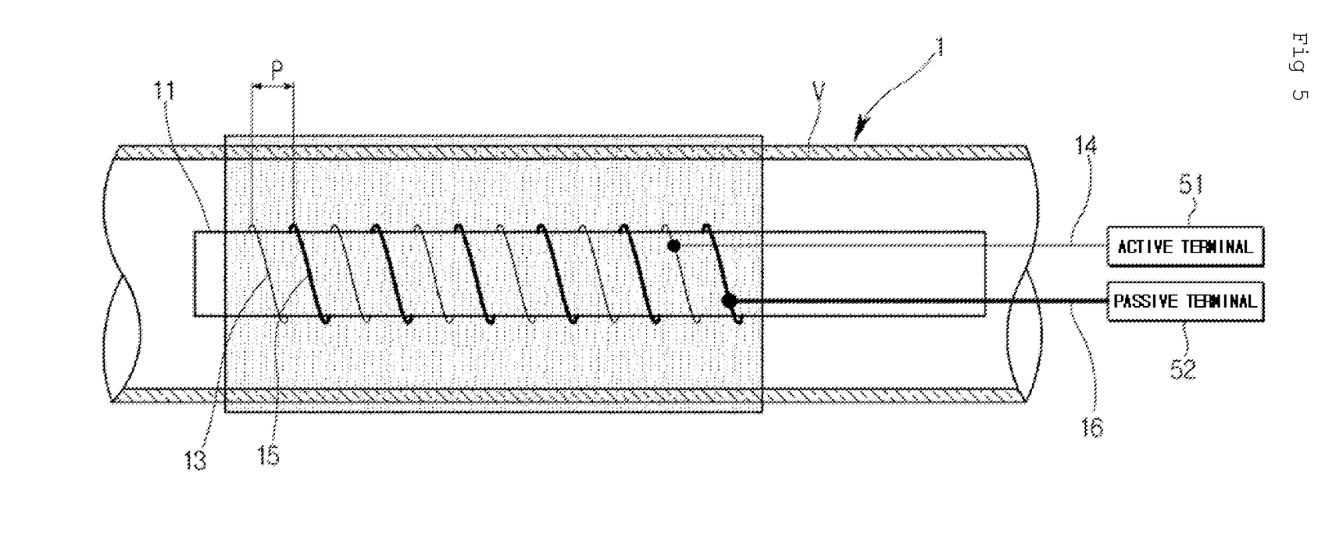
FIG. 5 is a diagram illustrating a heat generation range generated due the high-frequency energy radiation in the state in which the electrode illustrated in FIG. 4 is disposed around a lesion of a blood vessel.

Meanwhile, as illustrated in FIGS. 3 to 5, the electrode 1 according to the present invention is configured to include a body 11 inserted into tissues around a lesion and an active electrode body 13 and a passive electrode 15 which are wound around the body 11.

The body 11 has an elongated needle shape like a syringe needle as illustrated in FIG. 4 or has an elongated cylindrical pipe form as illustrated in FIG. 5, in which in the case of the needle-shaped body of FIG. 4, a tip portion of the body 11 is sharp to be easily inserted into tissues around a lesion and as illustrated in FIG. 3, the other end thereof is connected to the handle 2. To the contrary, when the body 11 is applied to a catheter in a cylindrical pipe form as illustrated in FIG. 5, the body 11 is connected to a tip portion of a moving wire.

Further, the active and passive electrode bodies 13 and 15 are a part which radiates a high frequency current generated from the high frequency generator 5 in the electrode 1 and as illustrated in detail in FIGS. 3 to 5, the active and passive electrode bodies 13 and 15 are each wound to be inclined in a spiral direction from a tip portion of an outer peripheral surface of the body 11 toward the back end. In this case, the two electrode bodies 13 and 15 are wound at the same lead angle in parallel at least twice or more and among those, as illustrated, the active electrode body 13 has the other end connected to an active terminal 51 of the high frequency generator 5 through an active line 14 of the electrode wire and the passive electrode body 15 has the other end connected to a passive terminal 52 of the high frequency generator 5 through a passive line 16 of the electrode wire 3. In this case, the active terminal 51 or the passive terminal 52 may be a positive pole or a negative pole according to convenience.

In particular, as illustrated in FIGS. 4 and 5, in the electrode 1 according to the present invention, since the passive electrode body 15 is also wound to be inclined through the active electrode body 13 wound in a spiral direction, the active electrode body 13 and the passive electrode body 15 keep a gap from each other, and thus heat generation starts around an intermediate point of a pitch P of each electrode body 13 and 15 at the time of radiating the high frequency energy. In this case, since the pitch P is shorter than a diameter of the body 11, the heat generation range has a cylindrical shape enclosing the body and more preferably, when the pitch P between the electrode bodies 13 and 15 is constant as illustrated in FIGS. 4 and 5, that is, when an alternating gap between the electrode bodies 13 and 15 is constant, the heat generation range has a cylindrical shape of which a longitudinal section is a rectangle as illustrated in FIG. 5.

Figure 6:
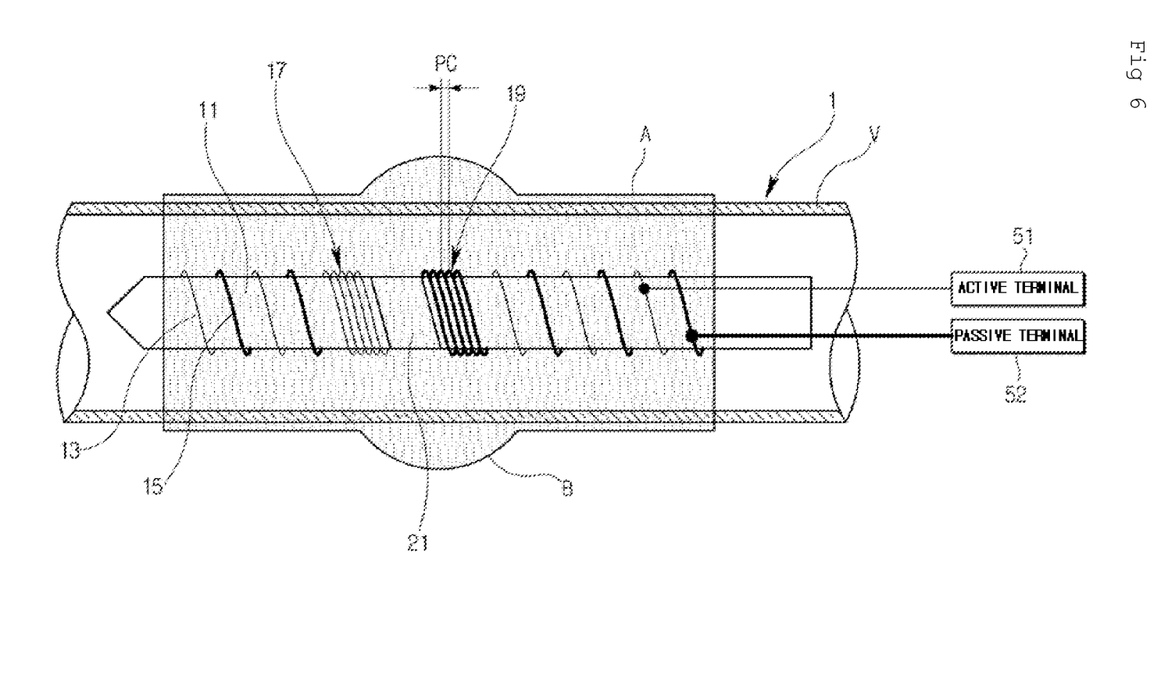
FIG. 6 is a diagram illustrating an electrode according to another embodiment of the present invention, along with a heat generation range.
Figure 7:
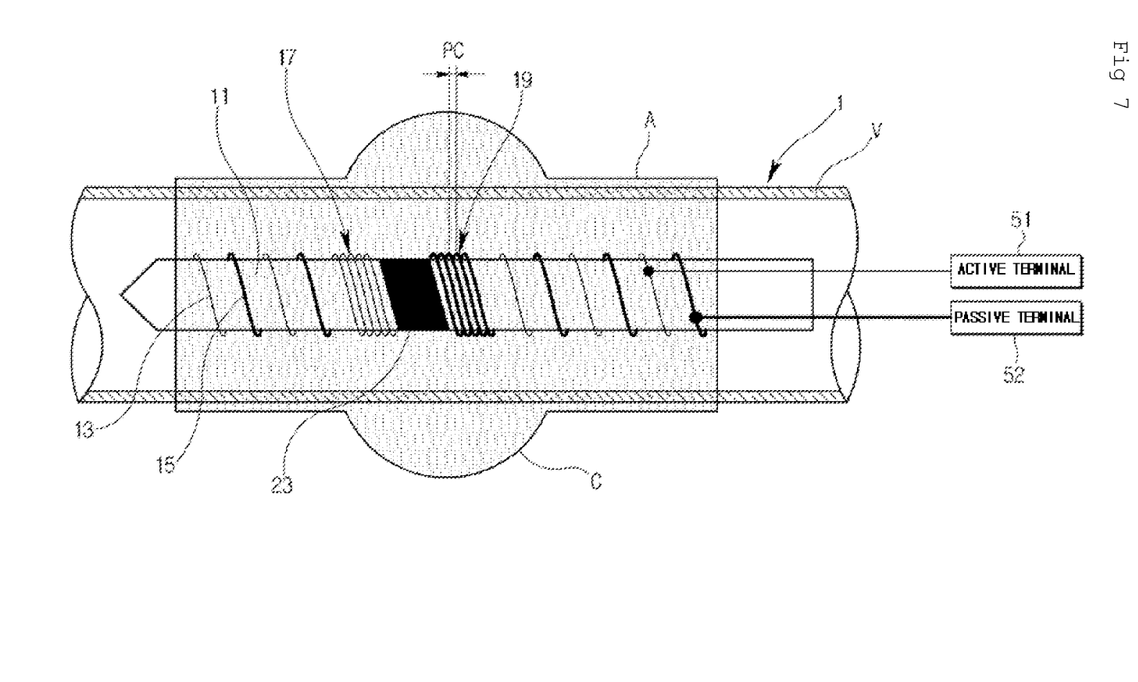
FIG. 7 is a diagram illustrating an electrode according to still another embodiment of the present invention, along with a heat generation range.

Further, in the electrode 1 according to another embodiment of the present invention, as illustrated in FIGS. 6 and 7, more than one concentration part 17 and 19 may be formed while one-to-one matching the active electrode body 13 and the passive electrode body 15. As illustrated, the concentration parts 17 and 19 of each of the active electrode body 13 and the passive electrode body 15 are formed at a position at which they match the passive electrode body 15 or the active electrode body 13, and therefore, unlike the other portion of the electrode bodies 13 and 15, one electrode is continuously wound without alternating with the other electrode.

In this case, in order to increase an emission density of high frequency energy, as illustrated in FIGS. 6 and 7, each of the concentration parts 17 and 19 is wound around the outer peripheral surface of the body 11 at an interval of the pitch P of the electrode bodies 13 and 15 which is denser than that of the pitch P of the other portion of the electrode bodies 13 and 15, preferably, without the interval of the pitch, that is, gapless.

As described above, each of the concentration parts 17 and 19 may not be considered as one winding body since the pitch P of a winding is short or is not present, such that as illustrated in FIG. 6, as another embodiment, an insulating gap 21 is secured between the concentration parts 17 and 19, thereby increasing the high frequency energy radiation efficiency.

In addition, as another embodiment, when an insulating part 23 is formed on the outer peripheral surface of the body 11 between the corresponding concentration parts 17 and 18, that is, of the insulating gap as illustrated in FIG. 7, even though the insulating gap 21 between the corresponding concentration parts 17 and 19 is not sufficiently secured as illustrated in FIG. 6, the insulating part 23 may keep insulating performance, thereby increasing the high frequency energy radiation efficiency.

Hereinafter, an action of the overlapping bipolar electrode 1 for high-frequency heat treatment according to the present invention configured as described above will be described.

Likewise the general bipolar electrode, the electrode according to the present invention necrotizes tissues around a lesion, which is to be operated, using high-frequency energy radiation and may maximize the effect when being used to be stuck into a targeted lesion as well as inserted into, in particular, a tubular organ V such as a blood vessel as illustrated in FIG. 5.

That is, the electrode 1 according to the present invention is useful to perform an operation on a lesion of the tubular organ such as a blood vessel. The reason is that the electrode 1 according to the present invention may restrictively and effectively cauterize the lesion generated in a cylindrical shape in the tubular organ V using the high frequency current radiated in the cylindrical shape as represented by A in FIG. 5.

To this end, the electrode 1 is inserted into the tubular organ as soon as the operation starts to find out the lesion, moves in parallel along a center of the tubular organ by the electrode apparatus 10, and is disposed at an accurate targeted position, that is, a lesion by a mark means such as an X-ray marker (not illustrated). When the disposition of the electrode 1 is confirmed, the high frequency generator 5 is operated to radiate the high frequency alternating current. In the case of the embodiment illustrated in FIGS. 4 and 5, the active electrode body 13 and the passive electrode body 15 radiate the high frequency energy between adjacent electrodes to the interval of the pitch P and an electrode as described above to form a high frequency energy radiation zone in a general cylindrical shape as represented by A. Therefore, the two electrode bodies 13 and 15 vibrate ions of the lesion by the energy generated in the radiation zone to generate friction heat and thus increase a temperature of tissues around the lesion, such that the lesion of the tubular organ may be effectively operated at a minimum thickness by the cylindrical radiation zone following the form of the lesion, that is, without the damage of other adjacent tissues.

Further, according to the electrode 1 according to another embodiment of the present invention, as illustrated in FIGS. 6 and 7, the heat generation range in a cylindrical shape, that is, the heat generation range having a longitudinal section in a rectangular shape is formed by the electrode bodies 13 and 15 and in addition, the heat generation range in an oval shape (represented by B of FIG. 6 and C of FIG. 7) based on the insulating gap 21 or the insulating part 23, that is, the heat generation range having a longitudinal section in an oval shape is formed at least one depending on the number of a pair of corresponding concentration parts 17 and 19. Therefore, even in the case of the lesion having a portion which is widely distributed out of the tubular shape, that is, even in the case in which a lesion widely distributed in a radius direction of a blood vessel occurs at a specific position while being distributed as a whole in the tubular tissue such as a blood vessel in a longitudinal direction, the concentration parts 17 and 19 match the lesion widely distributed in a radius direction, thereby effectively performing the cauterization.

INDUSTRIAL APPLICABILITY

Therefore, according to the overlapping bipolar electrode for high-frequency heat treatment according to the present invention, the bipolar electrode is overlappingly disposed on the body of the electrode in a spiral form to make the heat generation range by the high-frequency energy radiation generated between the adjacent corresponding active electrode body and passive electrode body be a cylindrical shape, and thus the heat generation range by the electrode matches the lesion of the tubular tissue such as, in particular, a blood vessel in terms of a form, thereby minimizing the damage of the adjacent normal tissue generated around the cauterization part at the time of cauterizing the lesion of the tubular tissue, reducing the cauterization omission part generated at both ends of the cauterization part, and remarkably improving the heat treatment efficiency by the electrode.

Further, since each of the concentration parts are disposed at a position where they correspond to one side of the active electrode body and the passive electrode body, the cylindrical heat generation range is formed by both electrodes as described above and the oval heat generation range extended in a radius direction of the tubular tissue is added at a point where the concentration parts are positioned, such that the lesion of the tubular tissue may be uniformly cauterized as a whole and the widely distributed specific portion may be widely cauterized in a wider range, thereby more improving the heat treatment efficiency on the tubular tissue.

The invention claimed is:

1. An overlapping bipolar electrode for high-frequency heat treatment, comprising:
   a cylindrical electrode body;
   an active electrode body configured to be connected to a first terminal of a high frequency generator while being wound around one side of an outer peripheral surface of the cylindrical electrode body several times; and
   a passive electrode body configured to be connected to a second terminal of the high frequency generator while being wound around the one side of the outer peripheral surface of the cylindrical electrode body alternately with the active electrode body several times;
   wherein the active electrode body and the passive electrode body are wound in a spiral form around the outer peripheral surface of the cylindrical electrode body at a constant alternating gap therebetween; and wherein the active electrode body and the passive electrode body each include continuously overlapping concentration parts without any one electrode body thereof alternating with the other electrode body thereof and the concentration parts are wound around the outer peripheral surface of the cylindrical electrode body at a denser gap than the alternating gap of the electrodes or gapless.

2. The overlapping bipolar electrode of claim 1, wherein an insulating gap is formed between the concentration part of the any one electrode body and the concentration part of the other electrode body.

3. The overlapping bipolar electrode of claim 2, wherein the outer peripheral surface of the cylindrical electrode body corresponding to the insulating gap is provided with an insulating part.

* * * * *